(12) United States Patent
Curry et al.

(10) Patent No.: US 7,280,261 B2
(45) Date of Patent: Oct. 9, 2007

(54) METHOD OF SCANNING AND LIGHT COLLECTION FOR A RARE CELL DETECTOR

(75) Inventors: Douglas N. Curry, Palo Alto, CA (US); Richard H. Bruce, Los Altos, CA (US); Robert T. Krivacic, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 11/017,440

(22) Filed: Dec. 20, 2004

(65) Prior Publication Data

US 2006/0132878 A1 Jun. 22, 2006

(51) Int. Cl.
*G02B 26/08* (2006.01)
(52) U.S. Cl. ...................................... 359/198
(58) Field of Classification Search ......... 359/198–200
See application file for complete search history.

(56) References Cited

U.S. PATENT DOCUMENTS

| | | | |
|---|---|---|---|
| 4,002,829 A | 1/1977 | Hutchison | |
| 4,010,364 A | 3/1977 | Fuwa | |
| 4,556,903 A | 12/1985 | Blitchington et al. | |
| 4,600,951 A | 7/1986 | Blitchington | |
| 4,721,851 A | 1/1988 | Kogure | |
| 4,849,645 A | 7/1989 | Mendenko et al. | |
| 4,875,780 A | 10/1989 | Moran et al. | |
| 4,941,719 A | 7/1990 | Hisada et al. | |
| 5,017,798 A | 5/1991 | Murakami et al. | |
| 5,216,485 A * | 6/1993 | Bird et al. ................... | 356/394 |
| 5,220,617 A | 6/1993 | Bird et al. | |
| 5,315,993 A | 5/1994 | Alcala | |
| 5,471,066 A | 11/1995 | Hagiwara | |
| 5,627,365 A | 5/1997 | Chiba et al. | |

(Continued)

FOREIGN PATENT DOCUMENTS

GB     1 579 188    11/1980

(Continued)

OTHER PUBLICATIONS

Bianchi, Diana W., et al., Fetomaternal Cellular and Plasma DNA Trafficking, The Yin and the Yang, *Annals New York Academy of Sciences*, pp. 119-131.

(Continued)

*Primary Examiner*—Euncha P. Cherry
(74) *Attorney, Agent, or Firm*—Fay Sharpe LLP

(57) ABSTRACT

An apparatus images a surface. An imager stage has a planar surface for supporting a sample. A fiber optic bundle has a first end of parallel first fiber ends that are arranged to define an input aperture for viewing the sample on the imager stage. A distal bundle end is arranged to define an output aperture disposed away from the imager stage. A scanning radiation source scans a radiation beam along a path that is perpendicular to the sample on the imager stage. The input aperture of the fiber optic bundle receives a light signal that is produced by the radiation source scan of the imager stage sample. The light signal is transmitted to the bundle output aperture. A photodetector detects the light signal at the distal bundle end, and a processor processes the detected light.

19 Claims, 8 Drawing Sheets

U.S. PATENT DOCUMENTS

| | | | |
|---|---|---|---|
| 5,640,246 | A | 6/1997 | Castonguay |
| 5,651,047 | A | 7/1997 | Moorman et al. |
| 5,732,162 | A | 3/1998 | Curry |
| 5,798,831 | A | 8/1998 | Hagiwara |
| 5,892,577 | A | 4/1999 | Gordon |
| 6,445,451 | B1 | 9/2002 | Douglas-Hamilton et al. |
| 6,545,334 | B2 | 4/2003 | Verhaegen |
| 6,582,363 | B2 | 6/2003 | Adachi et al. |
| 6,636,623 | B2 | 10/2003 | Nelson et al. |
| 2001/0046712 | A1 | 11/2001 | Hang et al. |
| 2002/0177885 | A1 | 11/2002 | Eisfeld et al. |
| 2002/0186368 | A1 | 12/2002 | Rosengaus et al. |
| 2004/0071330 | A1 | 4/2004 | Curry |
| 2004/0071332 | A1 | 4/2004 | Curry |
| 2004/0131241 | A1 | 7/2004 | Curry et al. |

FOREIGN PATENT DOCUMENTS

| | | |
|---|---|---|
| JP | 4296642 | 10/1992 |
| JP | 6148085 | 5/1994 |
| JP | 9145631 A | 6/1997 |

OTHER PUBLICATIONS

Wolfe, Josh, A Thousand Dots of Light, *Forbes/Wolfe Nanotech Report*, May 29, 2002, www.Forbes.com.

Pertl, Barbara, MD, et al., Fetal DNA in Maternal Plasma: Emerging Clinical Applications, *The American College of Obstetricians and Gynecologists*, Published by Elsevier Science Inc., vol. 98, No. 3, Sep. 2001, pp. 483-490.

Bauer, Kenneth D., et al., Reliable and Sensitive Analysis of Occult Bone Marrow Metastases Using Automated Cellular Imaging, *Clinical Cancer Research*, vol. 6, pp. 3552-3559, Sep. 2000.

Witzig, Thomas E., et al., Detection of Circulating Cytokeratin-positive Cells in the Blood of Breast Cancer Patients Using Immunomagnetic Enrichment and Digital Microscopy, *Clinical Cancer Research*, vol. 8, 1085-1091, May 2002.

Ghossein, R.A., et al., Molecular Detection and Characterisation of Circulating Tumour Cells and Micrometastases in Solid Tumours, *European Journal of Cancer* 36 (2000) 1681-1694, Mar. 2000, Elsevier Science Ltd.

Flatmark, Kjersti, et al., Immunomagnetic Detection of Micrometastatic Cells in Bone Marrow of Colorectal Cancer Patients, *Clinical Cancer Research*, vol. 8, 444-449, Feb. 2002.

Méhes, Gábor, et al., Quantitative Analysis of Disseminated Tumor Cells in the Bone Marrow by Automated Fluorescence Image Analysis, *Cytometry (Communications in Clinical Cytometry)*, 42:357-362 (2000, Wiley-Liss, Inc.

Werther, M., et al., The Use of the CELLection Kit in the Isolation of Carcinoma Cells from Mononuclear Cell Suspensions, *Journal of Immunological Methods*, 238 (2000) 133-141, 2000 Elsevier Science B.V.

Burchill, SA, et al., Comparison of the RNA-Amplification Based Methods RT-PCR and NASBA for the Detection of Circulating Tumour Cells, *2002Cancer Research Campaign, British Journal of Cancer* (2002) 86, 102-109.

European Search Report, dated Apr. 5, 2006; EPC Application No. 05112479.0-2204.

European Search Report, dated Jun. 2, 2006; EPC Application No. 05112370.1-2204.

\* cited by examiner

METHOD OF SCANNING AND LIGHT COLLECTION FOR A RARE CELL DETECTOR

CROSS REFERENCE

The following co-pending applications, U.S. Ser. No. 10/271,347, filed Oct. 15, 2002, and U.S. Ser. No. 10/616,366 filed Jul. 9, 2003, are hereby both incorporated herein in their entirety.

BACKGROUND OF THE INVENTION

The present exemplary embodiments relate to the imaging arts, and find particular application in conjunction with low and high-density cell detection, locating, and identifying in blood smears, biological assays, and the like across distinct imaging systems, and will be described with particular reference thereto. However, it is to be appreciated the exemplary embodiments will also find application in imaging, locating and identifying other types of low or high-density features on various substantially planar surfaces and samples, such as imaging semiconductor wafers, imaging particulate contaminants in fluids or thin solid films, and so forth, with such imaging finding specific uses in the printing arts, electronic arts, medical arts, and other scientific and engineering areas.

In rare cell studies, a particular problem arises due to the typically low concentration of the rare cells in the blood or other body fluid. In a typical rare cell study, blood is processed to remove cells that that are not needed. Then a fluorescent material is applied that attaches to antibodies, which in turn selectively attach to a cell surface or cellular protein of the rare cells. The cellular proteins may be membrane proteins or proteins within a cell, such as cytoplasm proteins. The antibodies may also attach to other types of molecules of the rare cell, as well as to DNA.

The fluorescent material may be a fluorescent marker dye or any other suitable material which will identify the cells of interest. A smear treated in this manner, which may include the blood and/or components of the blood, is prepared and optically analyzed to identify rare cells of the targeted type. For statistical accuracy it is important to obtain as large a number of cells as required for a particular process, in some studies at least ten rare cells should be identified, requiring a sampling of at least ten million cells, for a one in one-million rare cell concentration. Such a blood smear typically occupies an area of about 100 cm2. It is to be understood, however, that this is simply one example and other numbers of cells may be required for statistical accuracy for a particular test or study. Other cell identifiers which are being used and investigated are quantum dots and nano-particle probes. Also, while a rare cell is mentioned as a one-in-one-million cell concentration, this is not intended to be limiting and is only given as an example of the rarity of the cells being sought. The concepts discussed herein are to be understood to be useful in higher or lower levels of cell concentration.

In this regard, the ability to scan large numbers of cells at a high rate is considered a key aspect which increases the throughput of testing processes. Therefore, it is considered valuable to provide a system which improves the speed, reliability and processing costs which may be achieved by cell detection systems and/or processes.

Several-aspects may be considered as useful in increasing the throughput and reliability of scans at high rates of speed. For example, it would be useful to have a scanning system which permits high-speed scans in an accurate reliable manner, and a manner for increasing the accuracy with which cell detection occurs which includes decreasing a number of false or ghost images which may exist. While at the same time, maintaining or increasing the amount of data collected during a scan.

BRIEF DESCRIPTION OF THE INVENTION

In accordance with one aspect of the exemplary embodiments, an imager for imaging sample is disclosed. An imager stage has a planar surface that supports a sample. A light path has a first end arranged to define an input aperture. The input aperture provides for viewing the sample on the imager stage. A distal end is arranged to define an output aperture that is disposed away from the imager stage. A scanning radiation source is arranged to scan a radiation beam along a path that is perpendicular to the sample of the imager stage and proximate to the fiber light path. The scanning radiation source provides a substantially circular spot of illumination on the imager stage sample. The sample provides a light signal that is received by the input aperture and transmitted to the output aperture. A photodetector is arranged to detect the light signal at the distal end, and a processor processes the detected light signals.

In accordance with another exemplary embodiment, an image for imaging a generally planar surface is disclosed. A linearly translating stage linearly translates the surface in at least a first direction. A light path having a first end is arranged to define an input aperture for viewing the sample on the linearly translating stage. A distal end is arranged to define an output aperture that is disposed away from the imager stage. A polygon driven scanner is arranged to scan a beam along a path that is closely proximate the light path so that the beam interacts with the surface to produce a light signal. The light signal is collected by the input aperture and communicated to the output aperture. A photodetector is arranged to detect the light signal at the distal bundle end, and a processor processes the detected light signals.

In accordance with yet another exemplary embodiment, a method for imaging a sample is disclosed. A radiation beam is supplied perpendicular to the sample to be imaged. The perpendicular direction of the radiation beam is maintained as it sweeps along a scan path on the sample. At least some light produced by beam interaction with the sample is reflected in a direction orthogonally away from the sample. Collected light is detected at a selected output region. The sweeping, moving and detecting are coordinated to generate an array of picture elements representative of at least a portion of the sample.

BRIEF DESCRIPTION OF THE DRAWINGS

The embodiments may take form in various components and arrangements of components, and in various steps and arrangements of steps. The drawings are only for purposes of illustrating the embodiments.

DETAILED DESCRIPTION OF THE INVENTION

Figure 1:
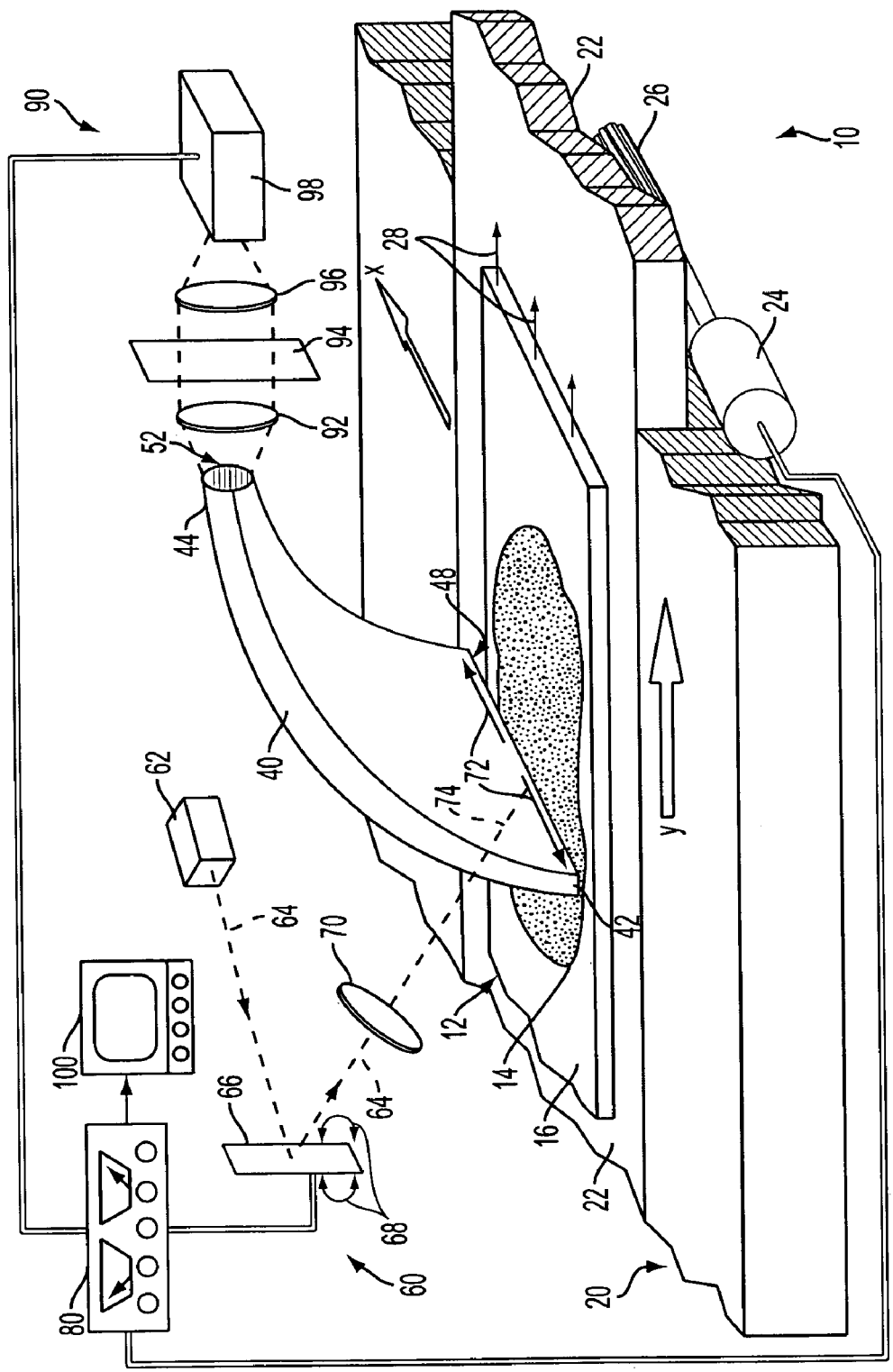
FIG. 1 shows a perspective view of an imaging apparatus formed in accordance with a further exemplary embodiment.

With reference to FIG. 1, an imaging apparatus or imager 10 examines a sample 12 such as a biological smear 14 disposed on at least a portion of a surface of a slide 16. Imaging apparatus or imager 10, as expanded upon below, is designed for detection of minute or microscopic material. It is to be appreciated that while the following discussion describes imager 10 in connection with specific material of certain sizes, it is not intended to be limited to use only in connection with these materials and these sizes, but rather is considered applicable to all materials and sizes, which would be detectable by the described device and method. Further, the imaging apparatus and imager are intended to include all appropriate image forming devices, including but not limited to a microscope and digital image.

As is known in the art, for cell studies the sample 12 is suitably prepared by drawing a sample of a biological fluid such as, but not limited to, blood or parts of blood from a subject. The fluid sample is treated with a fluorescent material, such as but not limited to a marker dye, that selectively bonds to a cell surface, cellular protein, or other element of the cell, optionally via an anti-body or other intermediary element. Suitable materials are known in the art for marking a number of different cell types of clinical interest, including selected cancer cell types, fetal cells, or other appropriate cells to be considered. The material preferably emits a characteristic luminescence, such as a fluorescence or a phosphorescence, responsive to a selected excitation irradiation, such as irradiation by a selected wavelength or spectrum of light, x-ray irradiation, electron-beam irradiation, or the like. The characteristic luminescence typically has a characteristic wavelength or spectral range of wavelengths.

The treated biological fluid is smeared onto a transparent slide using known techniques. In one suitable technique, a drop of the fluid is applied to the transparent slide 16, and an edge of a second transparent slide or other well-defined, clean edge is used to spread the drop across the slide 16. In another suitable technique, the fluid is applied while the slide 16 is being rotated by a spinner, so that centrifugal forces cause the fluid to smear out substantially uniformly over the slide 16. Other methods for preparing the biological smear can be substituted for the exemplary techniques.

The smear size will depend on the implementation, however, as an example, in one situation for a rare cell concentration of about one rare cell of interest per one million cells in the biological fluid, the smear 14 might contain at least ten million cells and occupy an area of about 100 cm$^2$. Of course, larger or smaller smears can be prepared which are suitable for the anticipated concentration of cells in the sample and the desired minimum measurable cell concentration.

The sample 12 is mounted on an imager translation stage 20 (shown in part) which includes a linearly translatable track 22 that supports the sample 12. A motor 24 connects with the track 22 via gearing 26 to translate the track 22 and the supported sample 12 along a y-direction (indicated by arrows 28). Although translation stage 20 driven by a rotary motor 24 is shown in FIG. 1, it is also contemplated to employ other types of mechanical driving devices. Furthermore, other types of sample movement such as sample rotation are also contemplated.

Figure 2:
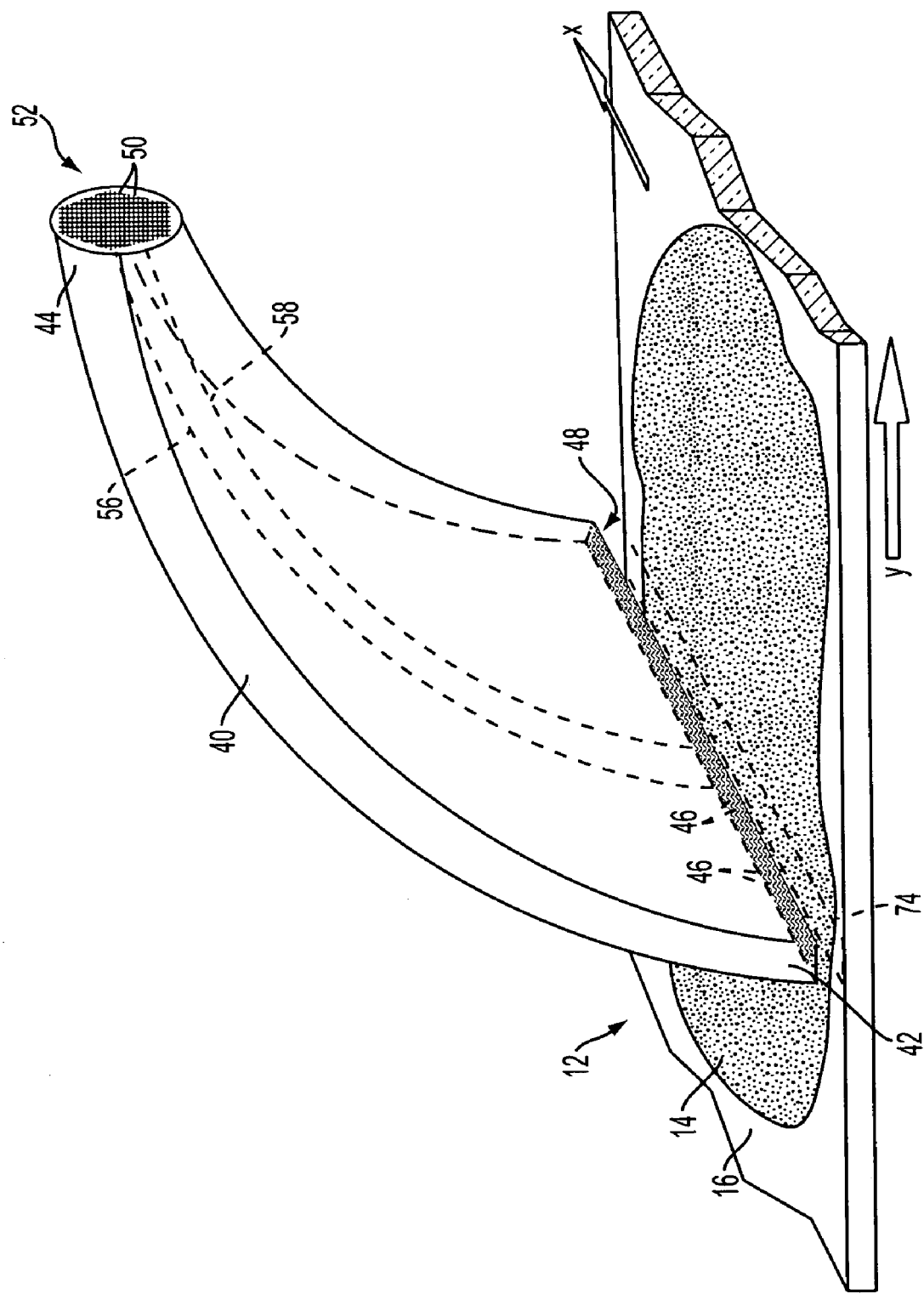
FIG. 2 shows an enlarged perspective view of the morphed fiberoptic bundle of the imaging apparatus of FIG. 1 in relation to the sample.
Figure 3:
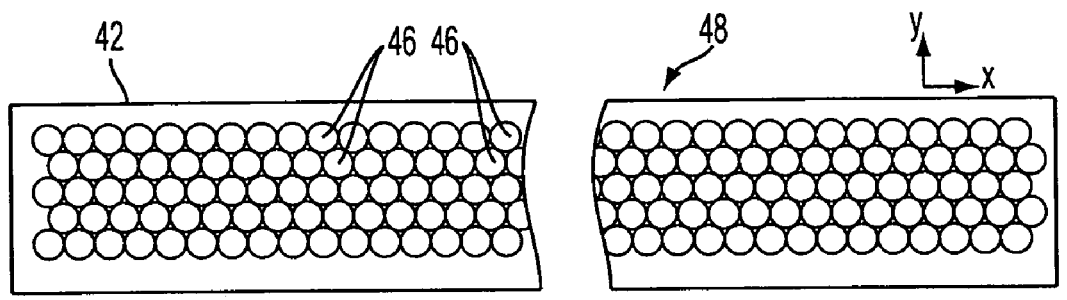
FIG. 3 shows an enlarged end view of the first end that defines the input aperture of the morphed fiber optic bundle of the apparatus of FIG. 1.

With continuing reference to FIG. 1 and with further reference to FIGS. 2 and 3, a light path such as fiber optic bundle 40 includes a first end 42 that is proximate to the sample 12, and a second end 44 that is distal from the sample 12. The first end 42 includes a plurality of first fiber ends 46 arranged substantially parallel to one another in an arrangement that defines a generally linear or high-aspect-ratio rectangular input aperture 48 (best seen schematically in FIG. 3) with a long dimension aligned with an x-direction. The input aperture 48 preferably includes a large number of first fiber ends 46, i.e. thousands of fiber ends. In one suitable embodiment, 40,000 fibers each having an approximately 50 micron diameter are arranged into a 40 fiber-by-1000 fiber array to define the input aperture 48 with a long dimension of approximately 5 cm and a short dimension of about 0.2 cm corresponding to a 25:1 aspect ratio. The first fiber ends 46 can be arranged in a regular pattern, as shown in FIG. 3. Alternatively, the first fiber ends can be arranged in an irregular or non-periodic array. Although generally round fiber ends are shown, it is also contemplated to employ fibers with oval, square, hexagonal, or other cross-sectional shapes. The first fiber ends 46 are oriented substantially perpendicular to the plane of the biological smear 14 so as to view the smear 14.

The optical fiber bundle 40 "morphs" or changes cross-sectional dimensions and shape between the first end 42 to the second end 44 such that the second end 44 includes a plurality of second fiber ends 50 (best seen schematically in FIG. 2) that define a compact, generally circular output aperture 52. Preferably, there is a one-to-one correspondence between the first fiber ends 46 and the second fiber ends 50, and each first fiber end connects with a second fiber end by an individual, distinct fiber having its own waveguiding cladding. Alternatively, each fiber can include only a light-transmissive fiber core, and an ambient/core interface functions to waveguide the light. Other optical fiber types can also be used, such fibers being well known in the art and typically formed of glass, plastic, or other light-transmissive materials by extrusion methods. In FIG. 2, the paths of two exemplary individual, distinct fibers 56, 58 are indicated as dotted lines. The morphed shape of the fiber bundle 40 from an extended, generally linear first end 42 to a compact, generally circular second end 44 is preferably formed by varying a spatial arrangement of the fibers of the optical fiber bundle 40 in a continuous fashion. For the exemplary 40,000 fiber embodiment with each fiber having a 50 micron diameter, the generally circular output aperture 52 has a circular diameter of about 1.3 cm.

It is particularly pointed out that the spatial relationship between the first fiber ends 46 and the second fiber ends 50 is generally arbitrary. For example, in FIG. 2 the fibers. 56, 58 run from approximately the same position in the input aperture 48. However, the fiber 56 terminates near a top of the output aperture 52, while the fiber 58 terminates near a middle of the output aperture 52. Although for convenience in arranging the fibers it is contemplated to arrange the first and second fiber ends 46, 50 in the respective apertures 48, 52 with a selected correspondence relative to one another, the fiber ends 46, 50 can instead have a generally uncorrelated and arbitrary relationship therebetween. Morphed fiber optic bundles similar to the fiber optic bundle 40 are known and used in the optical arts for other applications such as transforming focused light into a linear illumination pattern, and for coupling a light beam into a linear slit of a monochromator or spectrometer.

To obtain good light transmission, the fiber optic bundle 40 preferably has a high fiber packing factor, for example, fiber optic bundle 40 has a packing factor of about 0.80 or higher. Other factors influencing the light transmission include the polishing or light transmission properties of the tips of the first and second fiber ends 46, 50, the absorption per unit length of the fibers 56, 58, and the overall length of the fibers 56, 58. Fiber bending losses are preferably reduced by avoiding sharp bends of the fiber optic bundle 40. For example, as seen in FIGS. 1 and 2, the difference in orientation of the input aperture 48 and the output aperture 52 is achieved by a gradual bend in the optical fiber bundle 40. It is understood that while a fiber bundle has been described as the mode of transporting the acquired light, any other existing or subsequently developed light transmission element or light path or pipe which includes the appropriate characteristics may be employed.

With continuing reference to FIGS. 1-3, a scanning radiation (light) source 60 in a suitable embodiment includes a laser 62 that produces excitation light (radiation beam) 64 at a wavelength or wavelength range selected to excite the material used in marking the biological smear 14. The excitation light 64 is angularly scanned by a galvanometer 66 that has a reflective surface that rotates (indicated by curved arrows 68) responsive to an electrical input. An optional focusing lens 70 focuses the angularly scanned excitation light 64 onto the sample 12, and more particularly onto the biological smear 14. The angular scanning produced by the galvanometer 66 translates into a linear sweeping or scanning (indicated by arrows 72) of the excitation light on the biological smear 14 along a linear trajectory 74 arranged below the input aperture 48 and parallel to the long dimension of the input aperture 48. That is, using the coordinate system of FIG. 1 the linear trajectory 74 is parallel to the x-direction. In a suitable embodiment, the trajectory 74 is disposed on the biological smear 14 about one millimeter below the input aperture 48, although other distances will be appropriate dependant upon devices and the environment in which these concepts are implemented.

For cell studies, the excitation radiation 64 preferably produces a spot size on the biological smear 14 which substantially comports with a size of the cells, which may vary in size but are typically about one to thirty microns in size. To obtain such narrow beam focusing, the focusing lens 70 is typically included.

Electronic control unit 80 communicates with laser scanner 66 and the translation microscope stage 20 to raster the radiation beam 64 across the sample. Electronic control unit 80 identifies a beam sweep position as a first coordinate in the x-direction, and a position of the translation microscope stage 20 as a second orthogonal coordinate in the y-direction, to spatially map out the collected characteristic luminescence intensity as a function of position on sample 12. The x- and y-coordinates can be inferred from the laser scan velocity and stage translation velocities. The electronic control unit formats signal and spatial coordinates and displays an image representation on display 100 or the like.

With reference still on FIG. 1, a suitable signal detector 90 is arranged to detect the collected characteristic luminescence emanating from output aperture 52. A first lens 92 substantially collimates light. A light blocking filter 94 is optionally provided to remove scattered laser light from the collected light. A second lens 96 focuses the collimated collected light onto a photodetector arrangement 98.

Figure 4A:
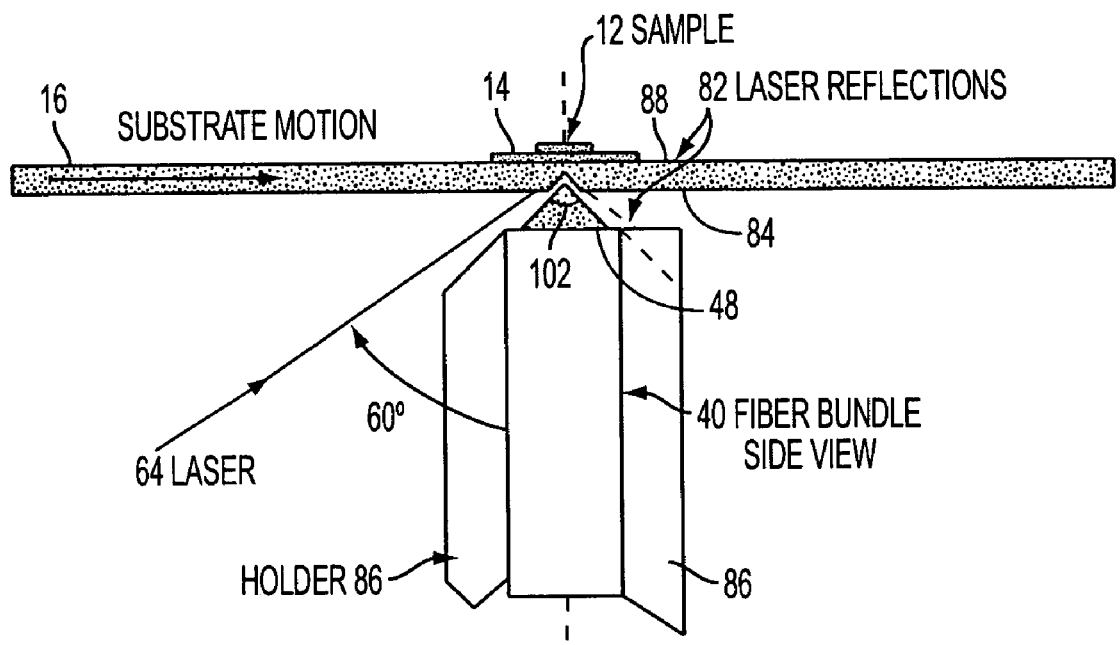
FIGS. 4A-4B shows a side view of the imaging apparatus of FIG. 1 centered on the first end of the morphed fiber optic bundle and an example of an elliptic illuminating spot.

With attention focused now on FIG. 4A and with continuing reference to FIG. 1, the angularly scanned excitation light 64 approaches the biological smear 14 or sample, 12 from a side orientation such that light hits a surface of glass slide 16 at an angle, typically about 60° off the normal. The input aperture 48 is set several millimeters away from the sample to allow room for the scanned field to enter from the side. The short axis is bisected by the scan line at 90°, or normal, to the substrate surface. Fluorescent excitation caused by the scanning illumination of sample 12 may fill an entire cone angle 102 of the input aperture 48. It has been determined that the laser spot illumination spans an elliptical area on the slide 16. When scanning from almost 60° off axis, the long axis of the ellipse is roughly twice the short axis. Hence, the resolution in the short axis is twice the resolution in the long axis. It has also been determined that the off-axis scanning causes the radiation beam 64 to reflect off the internal surface of the substrate. For example, in FIG. 4A, the input aperture 48 is arranged to view sample 12 from a side of slide 16 that is opposite the biological smear 14. The slide 16 is light transmissive for the characteristic luminescence of the cells. Excitation light 64 passes through the slide and impinges upon sample 12. When the light impinges the sample, reflected beam 82 reaches the first side of the slide at point 84. A portion of the reflected beam within the cone angle 102 transmits to the input aperture 48 of fiber bundle 40, while another portion transmits to a black surface such as bundle holder 86. A significant portion of the reflected light is reflected back through the slide to the surface that holds the sample at, for example, point 88. The imaging will view the actual sample at 12, but will also view a reflection of that sample at point 88. Indeed, a laser scan can make two or more bounces internally before illuminating a more distant location. This bouncing activity causes ghosting. The ghosting occurs because the distant location is ambiguously seen by the imaging system as being local. For example, when ghosting occurs, pairs of rare cells may be viewed when in fact a single rare cell is located.

Figure 4B:
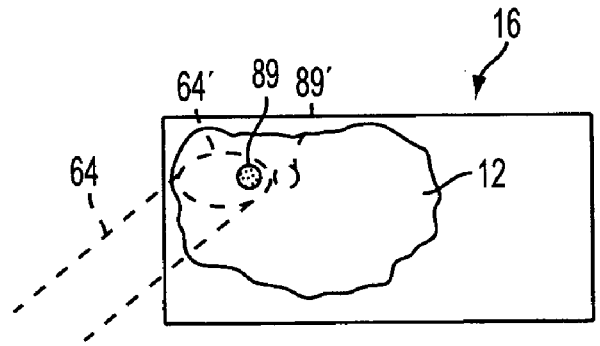

Turning to FIG. 4B, the concept of the elliptic illuminating spot and ghost images are discussed. It is noted the sizes of the elements are enlarged for ease of understanding. As beam 64 impinges on slide 16, elliptic spot 64' illuminates an elliptic area on slide 16. Due to the reflection described in FIG. 4A, not only will beam 64 illuminate an actual cell of interest 89, the multiple reflections can cause illumination of a ghost illumination 89' which may inappropriately be detected by the input aperture 48 as discussed in FIG. 4A. These ghost reflections are undesirable in a fast scanning operation as they act as noise, false positives, or other undesirable input during the detection process.

Figure 5:
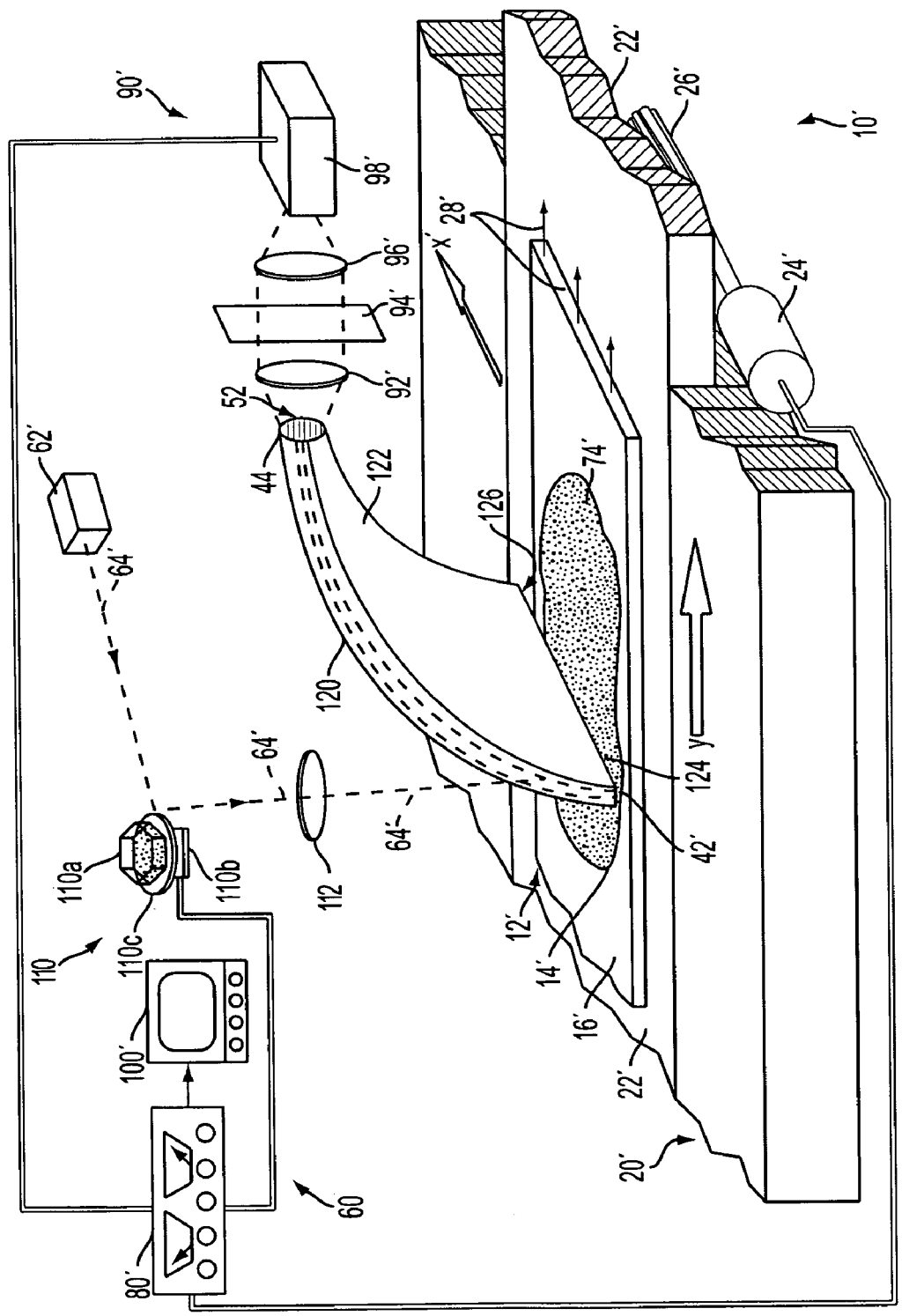
FIG. 5 shows a perspective view of another embodiment of an imaging apparatus formed in accordance with the present concepts.

With reference to FIGS. 5-8, an alternative configuration of the scanning radiation source is disclosed. In FIGS. 5-8, elements that correspond to similar elements of the embodiment of FIGS. 14 are indicated by primed reference numbers while new elements are indicated with unprimed reference numbers. The alterative configuration shown in FIGS. 5-8 is advantageously modified such that the laser scanning device 110 is situated so that the excitation light 64' that transmits from laser 62' is orthogonally directed to sample 12', i.e., it is supplied perpendicular or substantially at a 90° angle to-the surface of slide 16. Positioning the scanned field normal to the surface creates a more rounded spot instead of an elliptical spot when not at 90°, and ghosting is substantially reduced or eliminated. Reflected radiation from the sample 12' is on axis. Telecentric lens arrangement 112 is, optionally, arranged between laser scanner 110 and sample 12' to ensure the scan beam remains perpendicular to the sample surface. In addition, the rounded circular spot formed by the beam on the sample remains, in one embodiment, at a diameter of between about eight to ten microns as the beam is traversed along the width of the slide, such as when the beam is moved along the long or x-scan direction. It is to be appreciated that, for ease of understanding, FIG. 5 illustrates a conceptual arrangement of the scanning occurring in the long direction x'. It is understood that in this embodiment, beam 64' emits through the long length of the split fibers. It is to be appreciated that one of ordinary skill understands that such scanning could be accomplished in a number of ways, including bringing beam 64' between the fibers parallel to the sample, and then providing a mirror arrangement located between the split fibers configured to deflect the beam to the sample at 90°.

The laser scanner 110 represented on FIG. 5 can be selected from a variety of optical scanning devices. A polygon laser scanner advantageously provides a stable, even and predictable velocity. Spot movement along the sample is reliable and even when a polygon laser scanner is used. The polygon scanner provides for stability with closed loop speed control, and advantageously enables the scan system to perform at speeds beyond the 1 $cm^2$/sec speeds achieved by the galvanometer, commonly 4-6 times as fast.

The polygon laser scanner 110 of the present embodiment includes a plurality of reflecting mirrors 110a. The mirrors are actuated by an associated motor 110b. The motor permits for a linear increase and decrease in speed for smooth control of the movement of mirrors 110a. A flywheel 110c associated with the polygon scanner assists in maintaining speed uniformity of the scanner. Scanner arrangement 110, therefore, permits an increase and decrease in speed without an associated jitter which might otherwise occur in a scanning system employing an galvanometer. Particularly, in a galvanometer, the scanning mirror will move back and forth as opposed to the rotational action of the polygon system. This back and forth motion, requires an overcoming of inertia which may result in signal jitter. However, through the use of the mirror arrangement 110a, motor 110b, and flywheel 110c, jitter is substantially if not entirely eliminated from the system.

As will be further noted in FIG. 5, the laser scan reaches the sample 12 between two fiber bundles 120 and 122. Because the scanning is introduced perpendicular to the surface, the collection aperture of the fiber bundle is moved out of the scan field: As such, the fiber bundle disclosed in FIGS. 5-8 is bifurcated to form two separate fiber bundles 120 and 122. The fiber bundles are bifurcated at least along the first end 42' of the optical fibers to enable orthogonal scanning. The fiber bundle collection aperture is in two separate apertures because of the bifurcation. Input apertures 124 and 126 enable the fiber bundles to collect light from the scan line closely adjacent the line. Bifurcated bundles 120 and 122 merge to form output aperture 52' at the distal end 44' thereof.

Figure 6:
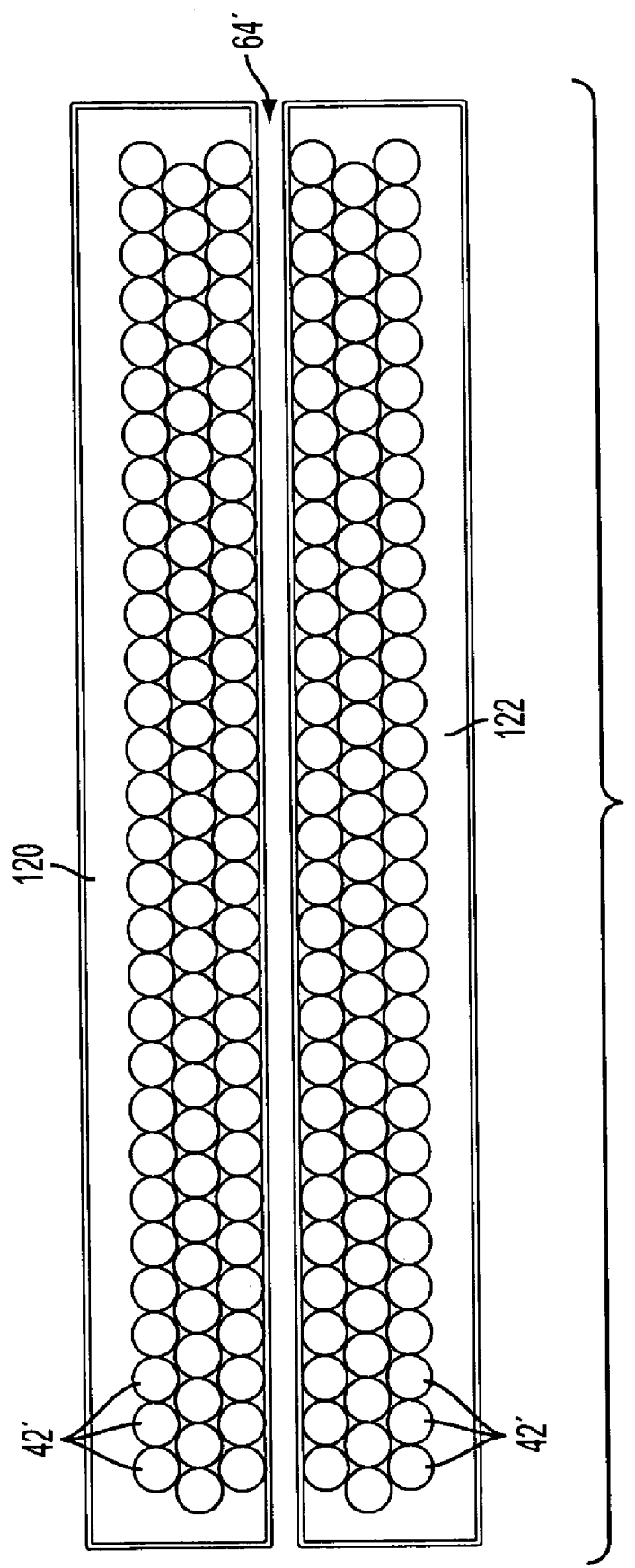
FIG. 6 shows an embodiment of an enlarged end view of the bifurcated fiber optic bundle of the apparatus of FIG. 5.

FIG. 6 schematically discloses the input aperture packing arrangement of the bifurcated fiber bundle with bundles 120 and 122. It is to be understood that FIG. 6 shows only a sub-set of all the fibers that might be used in an actual implementation. Because of the orthogonal scanning in this configuration, the bifurcated bundles are situated to be close to the scan line, as the reflection from the sample closely follows the scan line. As a result, the fiber bundles in FIGS. 5 and 6 are narrower in the x' direction than the corresponding bundle shown in input aperture of FIG. 3; The narrower bundles provide for a smaller input aperture and efficient light collection. The bundles can be arranged to cover the width of the slide. For example, the bifurcated bundle can be expanded longitudinally to match the width of the wellplate, for example, 2.66". The number of fibers remains the same as in FIGS. 1-4, with the exception that they are arranged differently and bifurcated. Because the area of the fiber collection is smaller, it is possible to conduct a wider scan along the surface. Scanning an orthogonal radiation beam is symmetrical, so it is advantageous to have the bifurcated bundles arranged on either side of the scan line 64' diametrically opposed or in another spaced relation. The scanning will also work with a single fiber optic bundle on one side of the scan line.

Figure 7:
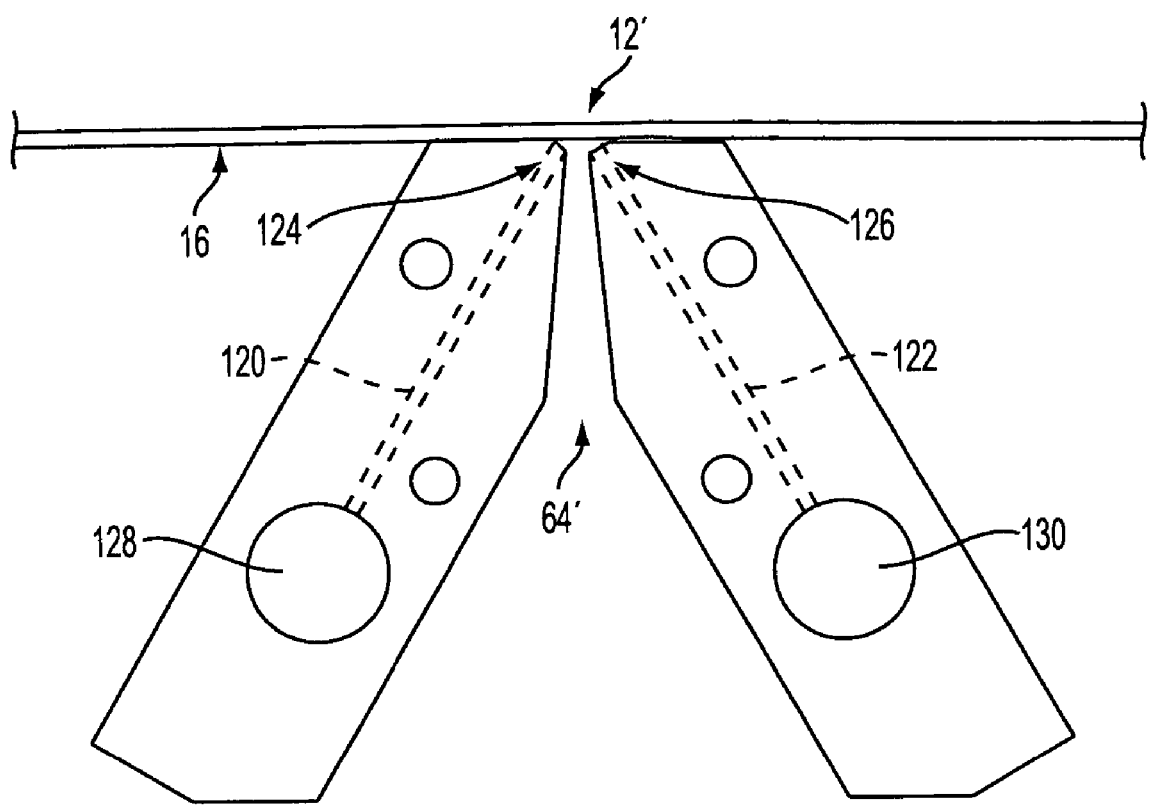
FIG. 7 diagrammatically shows another fiber optic bundle embodiment that is suitable for use in the apparatus of FIG. 5.

In another embodiment to FIG. 5, the bifurcated fiber optic bundles can alternatively have separate output apertures. Attention is directed to FIG. 7 which shows a scan field 64' which approaches the sample 12' perpendicular to a slide surface. Fiber bundles 120 and 122 are shown angled and offset from the scan axis to maximize the collective light reflecting from sample 12'. Because the bifurcated fiber optic bundles are smaller in width than those shown in FIG. 3, they are brought closer to the substrate surface without interfering with the scan field. The 0.66 NA collection cone can be entirely filled by fluorescent emission at the scan line. Input aperture openings 124 and 126 collect the emitted light. The light traverses the respective fiber bundles 120 and 122 to separate respective output apertures 128 and 130.

Separate output apertures 128, 130 can be separately filtered to view different frequencies of light. Thus, in the embodiments where the fiber optic bundles will have separate output apertures, the data collection scheme in FIG. 5 would be generally duplicated. Particularly two suitable signal detectors 90' would be arranged to detect each separate collected characteristic luminescent emanating from the output apertures 128 and 130. Two lens arrangements such as 92' collimate the individual light for each fiber, and separate light blocking filter arrangements 94' individually (and optionally) remove scattered laser light from the collected light. Thereafter, two second lens arrangements 96' focus the collimated light onto two separate photodetector arrangements 98'.

Figure 8:
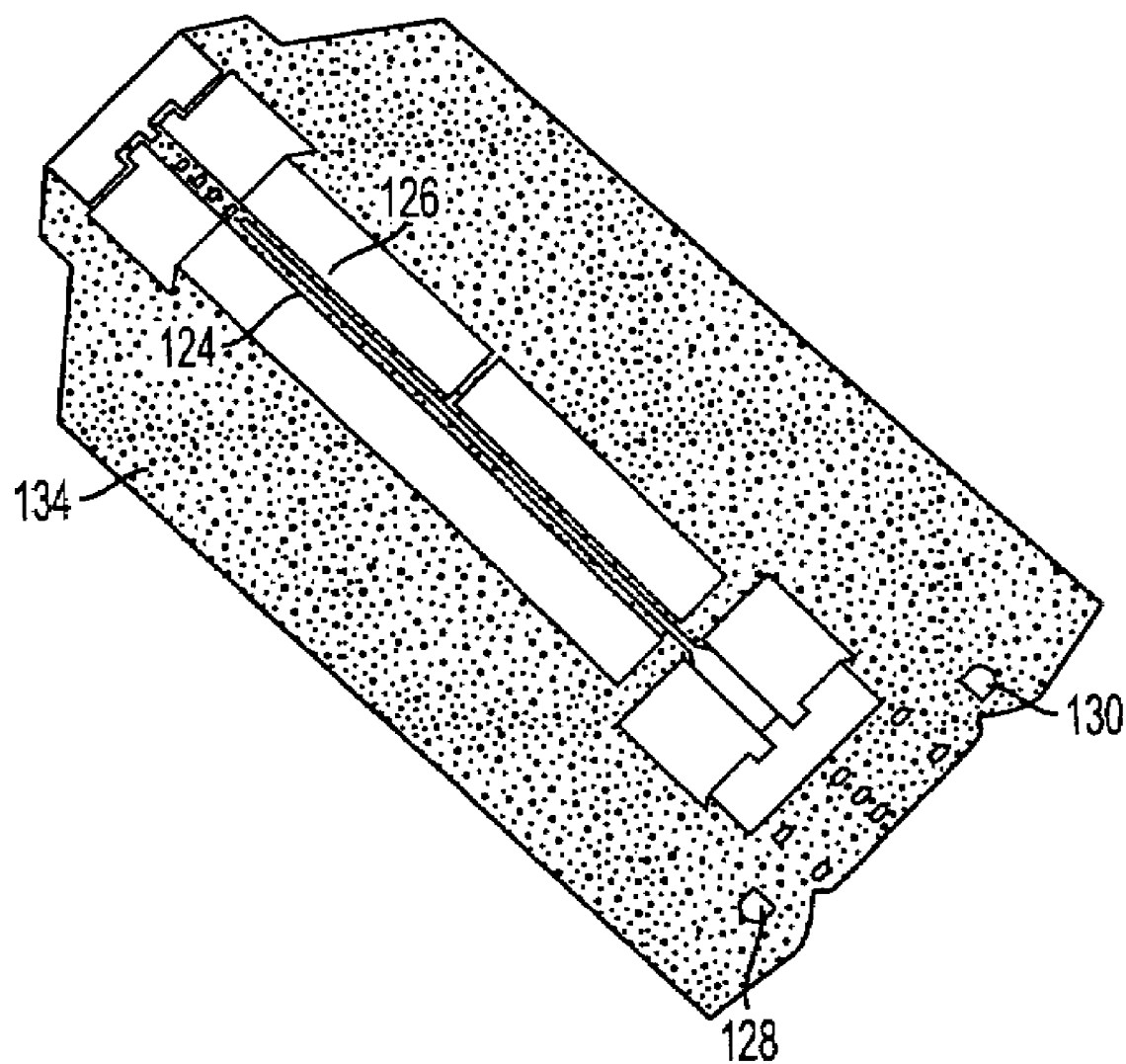
FIG. 8 is an embodiment of a fiber head that is suitable for use in the apparatus of FIG. 5.

A fiber head 134 is disclosed in FIG. 8. The two fiber bundle apertures 124 and 126 are shown along with a slit 114 for a scan field to emerge. The fiber head also shows fiber bundle exit ports 128 and 130.

Figure 9:
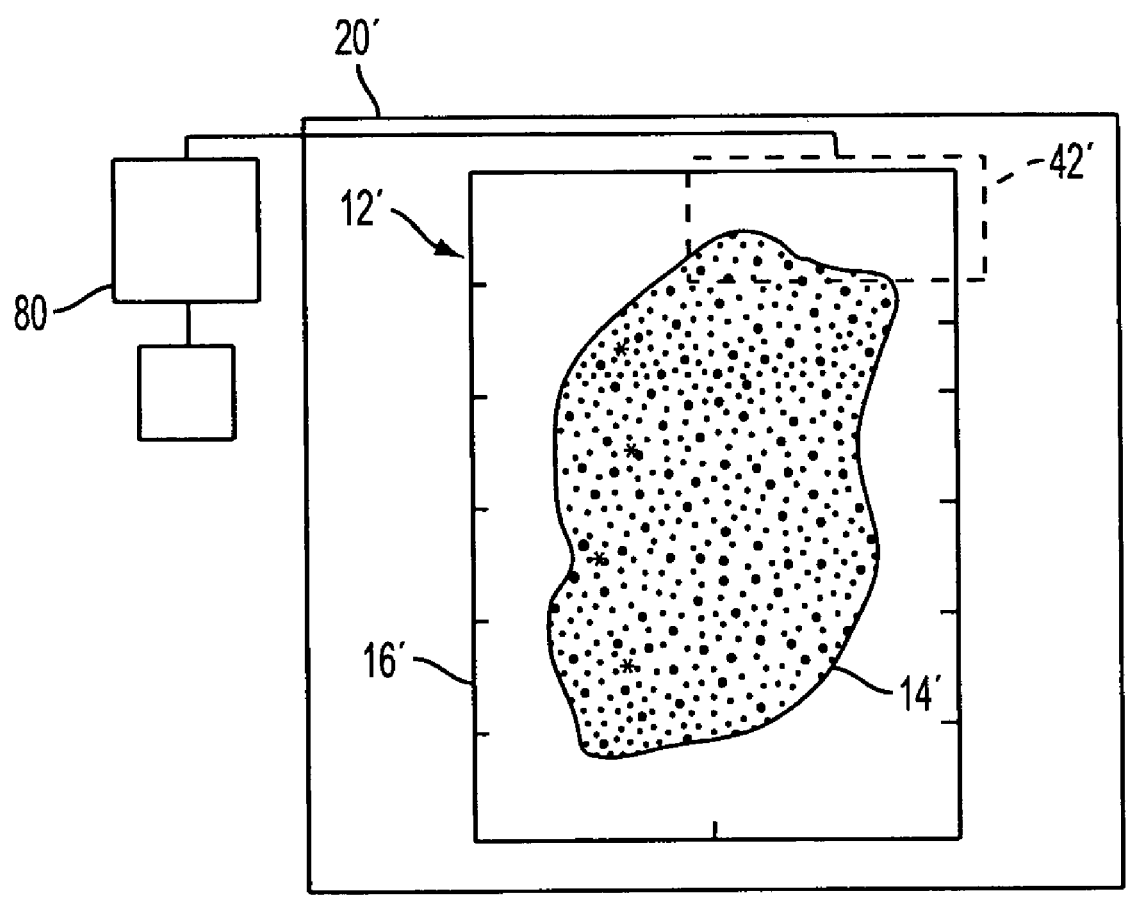
FIG. 9 is an embodiment which integrates an electronic microscope into the system of FIGS. 1 and 5.

Turning now to FIG. 9, in some instances the scanned sample will require processing following the identifying and localization of the cells of interest. At this point, the sample may be removed for these additional actions. For example, once the cells are localized, they can be analyzed for genetic defects using conventional analysis tools like fluorescence in situ hybridization (FISH), or by use of an automated fluorescent microscope, as well as by other investigative systems.

Alternatively, in other situations, a benefit will exist to undertake further investigation as part of the imaging systems of FIGS. 1 and 5 itself. One of these instances is when-the sample being investigated requires a higher resolution than may be obtained by the described system. Therefore, the system of the present application includes a further embodiment, wherein, as shown in FIG. 9, controller 80' provides the location or positional information of the sample cells 140-146 to an automated high-resolution device 148, such at an automated fluorescent microscope. Once the scanning process has been completed (or during the process), the automated high-resolution device 148 is provided with the cell position information and it is activated to move and investigate the cells in greater detail. Movement of automated high-resolution device 148 may be obtained by translation/gearing arrangements that are well known in the art. This embodiment finds particular application when it is known or highly suspected a certain cell will be found, for example, when a patient is undergoing treatment for cancer. In this, scenario, the integration of the high-resolution device 148 will increase the speed of review.

The present application suggests using a single laser for scanning images. It is foreseeable that additional lasers can be used because the use of separate bundles eases the addition of more filters. For example, two filters can be associated with each bundle. It is foreseeable that higher resolution will produce images with improved shape information and will enable better filtering of cells from artifacts. The number of objects that require subsequent microscopic scanning will be reduced accordingly.

The foregoing has been described with reference to exemplary embodiments. Obviously, modifications and alterations will occur to others upon reading and understanding the preceding detailed description. Accordingly, the appended claims as filed and as they may be amended are intended to embrace all such alternative, modifications, variations, improvements and substantial equivalents.

What is claimed is:

1. An imager for imaging a sample, the imager comprising:
    an imager stage having a planar surface for supporting a sample;
    a bifurcated light path having two fiber optic bundles, each bundle having a first end arranged to define an input aperture for viewing the sample on the imager stage, and a distal bundle end arranged to define an output aperture disposed away from the imager stage;
    a scanning source arranged to scan a beam along a path that is perpendicular to the sample on the imager stage and closely adjacent to both bundles of the bifurcated light path such that a substantially circular spot of illumination provided by the scanning source on the imager stage sample provides a light signal at least a portion of which is received by the input aperture of each bundle and transmitted via the bifurcated light path to the output aperture;
    a photodetector arranged to detect the light signal at the distal end; and
    a processor that processes the light signal detected by the photodetector.

2. The imager as set forth in claim 1, wherein the beam provided perpendicular to the sample is provided at substantially 90° to the sample surface.

3. The imager as set forth in claim 1, wherein the light signal provided to the input aperture is along a direction substantially normal to the imager stage surface.

4. The imager as set forth in claim 3, wherein the light signal is a fluorescence generated by interaction of the radiation beam with the sample.

5. The imager as set forth in claim 1, wherein the substantially circular spot of illumination provided by the scanning and radiation source reduces ghost images otherwise received by the input aperture.

6. The imager as set forth in claim 1, wherein the bifurcated light path has two fiber optic bundles, and wherein the input aperture of each bundle is arranged with the first fiber ends offset from a scan axis.

7. The imager as set forth in claim 4, further including:
    a collection cone situated to be filled by fluorescence emission from the sample.

8. The method according to claim 1, comprising:
    collecting light by fiber optic first ends of the bundles which are arranged substantially diametrically opposite each other about the radiation beam.

9. The method of claim 8, wherein the diametrically opposite bundles are offset from the scan axis of the radiation beam at equal but opposite angles.

10. The imager as set forth in claim 1, further including:
    a polygon laser scanner for scanning a radiation beam onto the imager stage surface.

11. The imager as set forth in claim 10, wherein the polygon laser scanner includes a plurality of mirrors rotated by a motor for rotating the mirrors.

12. The imager as set forth in claim 1, further including:
    an integrated microscope.

13. An imager for imaging a generally planar surface, the imager including:
    a linearly translating stage for translating a planar surface in at least a first direction;
    a bifurcated light path having two light path bundles, each bundle having a first end arranged to define an input aperture for viewing the sample on the linearly translating stage, and a distal end arranged to define an output aperture disposed away from the imager stage;
    a scanning source including a polygon driven scanner arranged to scan a beam along a path that is perpendicular and proximate to the sample surface such that the beam interacts with the sample surface to produce a substantially circular light signal a portion of which is collected by the input aperture of each bundle and communicated to the output aperture;
    a photodetector arranged to detect the light signal at the distal bundle end; and
    a processor that processes the light signal detected by the photodetector.

14. The imager as set forth in claim 13, wherein the polygon driven scanner is arranged to scan the radiation beam perpendicular to the sample surface.

15. The imager as set forth in claim 13, wherein the polygon driven scanner includes a plurality of mirrors rotated by a motor.

16. The imager as set forth in claim 15, wherein the motor is configured to linearly increase and decrease speed.

17. The imager as set forth in claim 13, further including:
    a telecentric lens for communicating the radiation beam from the polygon driven scanner to the surface to be scanned.

18. The imager as set forth in claim 14, wherein a telecentric lens bends the radiation beam to be perpendicular to the surface as the scan location changes.

19. A method for imaging a sample, comprising:
    supplying a substantially circular beam of radiation perpendicular to the sample;
    maintaining the perpendicular direction of the radiation beam as it sweeps along a scan path on the sample;
    reflecting at least some light produced by beam interaction with the sample in a direction away from the sample;
    collecting light produced by beam interaction with the sample in at least one proximate element of an array of fiber optic first ends;
    detecting collected light at a selected output region; and
    coordinating sweeping, moving and detecting to generate an array of picture elements representative of at least a portion of the sample.

* * * * *